United States Patent [19]

Glen et al.

[11] 4,056,635
[45] Nov. 1, 1977

[54] 2,6-DIISOPROPYLPHENOL AS AN ANAESTHETIC AGENT

[75] Inventors: John Baird Glen; Roger James, both of Macclesfield, England

[73] Assignee: Imperial Chemical Industries Limited, London, England

[21] Appl. No.: 559,880

[22] Filed: Mar. 19, 1975

[30] Foreign Application Priority Data

Mar. 28, 1974 United Kingdom ............. 13739/74

[51] Int. Cl.² ........................................... A61K 31/05
[52] U.S. Cl. ................................................. 424/346
[58] Field of Search ...................... 424/346, 168, 170

[56] References Cited

U.S. PATENT DOCUMENTS

| | | | |
|---|---|---|---|
| 2,104,412 | 1/1938 | Roselle | 260/612 D |
| 2,966,442 | 12/1960 | Elias et al. | 424/346 X |
| 3,067,106 | 12/1962 | Brown | 424/346 |
| 3,476,838 | 11/1969 | Ecke et al. | 424/346 X |

FOREIGN PATENT DOCUMENTS

| | | |
|---|---|---|
| 391,944 | 3/1962 | Japan. |
| 803,080 | 10/1958 | United Kingdom. |
| 831,071 | 3/1960 | United Kingdom. |

*Primary Examiner*—Allen J. Robinson
*Attorney, Agent, or Firm*—Cushman, Darby & Cushman

[57] ABSTRACT

Sterile pharmaceutical compositions for parenteral administration containing the compound 2,6-diisopropylphenol, and a method for producing anaesthesia in a warm-blooded animal by parenteral administration of said compound.

2 Claims, No Drawings

2,6-DIISOPROPYLPHENOL AS AN ANAESTHETIC AGENT

This invention relates to a pharmaceutical composition which may be administered parenterally to a warm-blooded animal for the production of general anaesthesia.

According to the invention there is provided a sterile pharmaceutical composition which comprises the compound 2,6-diisopropylphenol in association with a sterile pharmaceutically-acceptable diluent or carrier, the composition being suitable either directly or after dilution with a liquid diluent for parenteral administration to a warm-blooded animal.

The compound 2,6-diisopropylphenol is a known compound and may be obtained and purified by known means. It is liquid at laboratory temperature (m.p. 18° C.).

The composition of the invention is preferably an aqueous composition which comprises the compound 2,6-diisopropylphenol in sterile admixture with water and a surfactant or other solubilizing agent, and may optionally contain one or more additional solvents.

Alternatively, the composition of the invention may be an aqueous composition which comprises the compound 2,6-diisopropylphenol in sterile admixture with water and an additional water-miscible, non-aqueous solvent, the proportions of which are such that a homogeneous composition is obtained.

Yet alternatively the composition of the invention may be a liquid non-aqueous composition which comprises a sterile solution of the compound 2,6-diisopropylphenol in a suitable water-miscible, non-aqueous solvent, which solution may optionally contain a surfactant. Such a composition may be used directly for parenteral administration, especially to non-human animals, or it may be a concentrated solution suitable for dilution with sterile water, optionally containing a surfactant, the sterile diluted aqueous composition then being of the type described in either of the two preceding paragraphs.

Yet alternatively the composition of the invention may comprise a sterile solid or semi-solid mixture of 2,6-diisopropylphenyl with a solid diluent, for example lactose, saccharin sodium or a cyclodextran, which composition is suitable for dilution with a sterile aqueous diluent to form a composition of the type described in either of the two paragraphs preceding the last paragraph above.

Yet alternatively the composition of the invention may comprise an oil-in-water emulsion in which the 2,6-diisopropylphenol, either alone or dissolved in a water-immiscible solvent, for example a vegetable oil, for example arachis oil, or an ester of a fatty acid, for example ethyl oleate, is emulsified with water by means of a surfactant.

A suitable surfactant is, for example, a non-ionic surfactant, for example a condensation product of ethylene oxide with a fatty acid, for example a polyoxyethylene laurate, stearate or oleate, for example such a surfactant known under the Trade Mark 'Myrj'; or a condensation product of ethylene oxide with a vegetable oil, for example castor oil, or a derivative thereof, for example such a surfactant known under the Trade Mark 'Cremophor,' 'Micelliphor,' 'Texofor' D, 'Emulphor' (or 'Mulgofen'); or a condensation product of ethylene oxide with a long-chain aliphatic alcohol, for example a polyoxyethylene cetyl, lauryl, stearyl or oleyl ether, for example such a surfactant known under the Trade Mark 'Brij'; or a condensation product of ethylene oxide with a partial ester derived from a fatty acid and a hexitol anhydride, for example a polyoxyethylene sorbitan monolaurate, monopalmitate, monostearate or monooleate, for example such a surfactant known under the Trade Mark 'Tween'; or a polyoxyethylene-polyoxypropylene block copolymer, for example such a surfactant known under the Trade Mark 'Pluronic.'

Particular sufactants of the above types which may be used in a composition of the invention are those known under the Trade Mark 'Tween' 20, 40, 60 or 80; 'Myrj' 52 or 53; 'Brij' 35; 'Pluronic' F68; 'Emulphor' (or 'Mulgofen') EL 620 or EL 719; 'Texophor' D40 or D80; 'Cremophor' EL, RH40 or RH60 or 'Micelliphor,' and of these a preferred surfactant is 'Cremophor' EL, 'Cremophor' RH40, 'Micelliphor' or 'Pluronic' F68.

Other surfactants which may be used in a composition of the invention, especially if the composition is of an emulsion type, are naturally occurring phosphatides, for example lecithin, or esters of a hexitol anhydride and a fatty acid, for example a sorbitan monolaurate, monopalmitate, monostearate or monooleate, for example such a surfactant known under the Trade Mark 'Span.'

A suitable solubilizing agent other than a surfactant is, for example, polyvinylpyrrolidone, saccharin sodium or a cyclodextran.

A suitable additional solvent in an aqueous composition of the invention, or a suitable non-aqueous solvent which may be used in a liquid non-aqueous composition of the invention is, for example, an alcohol, for example ethanol; a glycol, for example propylene glycol, hexylene glycol or a polyethylene glycol, for example a polyethylene glycol of molecular weight approximately 200, 400, or 600; or a glycol monoether, for example ethylene glycol monoethyl ether; or a water-miscible ester or amide, for example γ-butyrolactone, ethyl lactate, N-methylformamide, N,N-dimethylacetamide, N-β-hydroxyethyllactamide or N,N,N',N'-tetramethylurea. A preferred solvent is ethanol, propylene glycol or a polyethylene glycol of molecular weight approximately 200, 400 or 600.

A preferred aqueous composition of the invention comprises from 0.1 to 5% by weight, especially from 1 to 2% by weight, and particularly 2% by weight, of 2,6-diisopropylphenol; from 2 to 30% by weight, especially from 10 to 20% by weight, of a non-ionic surfactant, and optionally from 2 to 30% by weight of an alcohol or glycol additional solvent, the rest of the composition being water.

A preferred composition of the invention which does not contain a surfactant comprises from 0.1 to 20% by weight, especially from 1 to 2% by weight, and particularly 2% by weight, of 2,6-diisopropylphenol; and from 10 to 99.9% by weight, especially 40 to 98% by weight, of a water-miscible solvent, the rest of the composition, if any, being water.

When an alternative solubilizing agent is used, this will be present in the composition in the range, for example, of from 20 to 40% by weight of polyvinylpyrrolidone, from 2 to 20% by weight of saccharin sodium or from 0.2 to 10% by weight of a cyclodextran.

The composition of the invention may optionally contain one or more additional constituents selected from stabilisers, preservatives and antioxidants, for example parabens derivatives, for example propyl p-hydroxybenzoate, butylated hydroxytoluene derivatives, ascorbic acid and sodium metabisulphite; metal ion sequestering agents, for example sodium edetate; and antifoaming agents, for example a silicone derivative, for example dimethicone or simethicone. The composition of the invention may also contain another anaesthetic agent.

An aqueous composition of the invention is preferably adjusted to a pH of between 4 and 10, especially between 5 and 7, and it may contain buffering agents, for example citric acid and sodium citrate, to maintain the pH value.

The composition of the invention may be made isotonic with blood by the incorporation of the required amount of a suitable inorganic salt, for example from 0.1 to 0.9% by weight sodium chloride, or of a sugar or sugar derivative, for example dextrose. Furthermore, a suitable sterile aqueous saline or dextrose solution may be used in place of sterile water wherever such water is hereinbefore or hereinafter mentioned.

A particularly preferred composition of the invention comprises a sterile aqueous composition containing from 1 to 5% by weight, especially from 1 to 2% by weight and particularly 2% by weight of 2,6-diisopropylphenol; from 10 to 20% by weight of a polyoxyethylene caster oil derivative, especially 'Cremophor' EL, 'Cremophor' RH40 or 'Micelliphor' or of a polyoxyethylene-polyoxypropylene block copolymer, especially 'Pluronic' F68; and optionally from 5 to 20% by weight of ethanol, propylene glycol or a polyethylene glycol, the rest of the composition being water or a suitable saline or dextrose solution. This composition will preferably be buffered to a pH of between about 5 and 7.

The composition may be sterilised by conventional techniques, for example by heat or irradiation, or by filtration through a bacterial filter, for example a cellulose ester membrane of pore size no greater than 0.22$\mu$.

The compound 2,6-diisopropylphenol produces smooth and rapid anaesthesia when injected intravenously as a composition of the invention into mice, rats, rabbits, cats, rhesus or pigtail monkeys, pigs, sheep, horses or cattle at a single dose of between 2.5 and 10 mg. per kg. bodyweight. Anaesthesia is produced in less than 1 minute and lasts, depending upon the species and the dose, from 3 to 25 minutes. Recovery of all animals is normal and rapid, depending upon the species and the dose taking from 7 to 45 minutes from induction, and no adverse side-effects are noted at anaesthetic doses. The $HD_{50}$ dose of the compound in mice is 13.5 mg. per kg. bodyweight and the $LD_{50}$ dose in mice is 56 mg./kg. bodyweight. The compound may also be administered intramuscularly.

The composition of the invention may be used for the induction of anaesthesia prior to maintenance with a conventional inhalation anaesthetic, or it may be used as a sole anaesthetic agent of short duration, or by repeated administration or by continuous infusion it may be used as a sole anaesthetic agent of longer duration.

When used for inducing anaesthesia in an adult human it is expected that a composition of the invention will be administered such that between 5 and 10 ml. of a composition containing between 1 and 5% by weight, preferably 2% by weight, of 2,6-diisopropylphenol is administered during between 15 and 30 seconds. When used in children, a composition containing 1% by weight of 2,6-diisopropylphenol is preferred.

A composition of the invention will usually be provided for use in a warm-blooded animal in unit dosage form, preferably in a sealed ampoule containing from 5 to 10 ml. of a liquid composition. The ampoule may contain the liquid under an atmosphere of nitrogen, and the contents of the ampoule may be made sterile either by bacterial filtration followed by use of an aseptic filling technique, or by heat treatment of the ampoule after sealing.

The invention is illustrated but not limited by the following Examples:

EXAMPLE 1

Distilled water is added to a solution of 2,6-diisopropylphenol (20 g.) in a polyoxyethylated ricinoleic acid (100 g. of 'Cremophor' EL) until a volume of 1 liter is obtained. The solution is filled into ampoules which are then sealed and sterilized by heating in a steam autoclave. There is thus obtained a sterile solution suitable for administration parenterally to a warm-blooded animal.

EXAMPLE 2

Distilled water (90 ml.) is added slowly to a well-stirred solution of 2,6-diisopropylphenol (2 g.) in 'Cremophor' EL (10 g.). The resulting micro-emulsion is passed through a bacterial filter and there is thus obtained a sterile composition suitable for parenteral administration to a warm-blooded animal.

The process described above is repeated except that there is incorporated into the mixture either
i. sodium edetate (0.02 g.); or
ii. citric acid (0.1 g.); or
iii. propyl p-hydroxybenzoate ('Nipasol' M, 0.01 g.; 'Nipasol' is a Trade Mark); or
iv. 2,6-di-t-butyl-4-methylphenol ('Topanol' BHT, 0.01 g.; 'Topanol' is a Trade Mark).

In each case there is obtained a sterile composition suitable for parenteral administration to a warm-blooded animal.

EXAMPLE 3

80 Ml. of a solution of sodium chloride (0.9 g.) and sodium edetate (0.02 g.) in distilled water (100 ml.) are added slowly to a well-stirred solution of 2,6-diisopropylphenol (2 g.) in a mixture of 'Cremophor' EL (10 g.) and ethanol (10 ml.). The micro-emulsion thus obtained is passed through a bacterial filter, and there is thus obtained a sterile composition suitable for parenteral administration to a warm-blooded animal.

The process described above is repeated except that citric acid (0.1 g.) is used in place of the sodium edetate. There is similarly obtained a sterile micro-emulsion suitable for parenteral administration to a warm-blooded animal.

EXAMPLE 4

Distilled water (80 ml.) is added slowly to a well-stirred solution of 2,6-diisopropylphenol (2 g.) in a mixture of 'Cremophor' EL (10 g.) and $\gamma$-butyrolactone (10 g.) The resulting micro-emulsion is passed through a bacterial filter and there is thus obtained a sterile composition suitable for parenteral administration to a warm-blooded animal.

EXAMPLE 5

Distilled water (900 ml.) is added slowly to a well-stirred solution of 2,6-diisopropylphenol (10 g.) in polyoxyethylene (20) sorbitan monooleate ('Tween' 80, 100 g.; 'Tween' is a Trade Mark). The resulting micro-emulsion is passed through a bacterial filter and there is thus obtained a sterile composition suitable for parenteral administration to a warm-blooded animal.

EXAMPLE 6

Distilled water (90 ml.) is added to a solution of 2,6-diisopropylphenol (2 g.) is polyoxyethylene (20) sorbitan monopalmitate ('Tween' 40, 10 g.). The emulsion thus obtained in repeatedly passed through a homogeniser until the particle size of the emulsion is reduced to an average of 5 microns, and the resulting micro-emulsion is sterilised by heating in an autoclave. There is thus obtained a sterile composition suitable for parenteral administration to a warm-blooded animal.

The process described above is repeated except that the 'Tween' 40 is replaced by an equal amount of polyoxyethylene (20) sorbitan monostearate ('Tween' 60). There is thus similarly obtained a sterile composition suitable for parenteral administration to a warm-blooded animal.

The process described above is repeated except that the ingredients used are:
a. 2,6-diisopropylphenol (1 g.); polyoxyethylene monostearate ('Myrj' 52) (5 g.); distilled water (95 ml.):
b. 2,6-diisopropylphenol (10 g.); polyoxyethylene monostearate ('Myrj' 53) (100 g.); distilled water (900 ml.).

There is similarly obtained a sterile composition suitable for parenteral administration to a warm-blooded animal.

EXAMPLE 7

Distilled water (80 ml.) is added to a stirred mixture of 2,6-diisopropylphenol (2 g.), 'Cremophor' EL (1 g.), 'Tween' 80 (1 g.) and arachis oil (20 ml.). The resulting emulsion is repeatedly passed through a homogenizer until a suitably low particle size is formed, and is then sterilized by heating in an autoclave. There is thus obtained a sterile composition suitable for parenteral administration to a warm-blooded animal.

EXAMPLE 8

The process described in Example 1 is repeated except that the 100 g. of 'Cremophor' EL are replaced by the indicated amount of one of the following surfactants:

| | |
|---|---|
| 'Cremophor' RH40 (200 g.) | |
| 'Micelliphor' (200 g.) | (polyoxyethylated castor oil derivatives) |
| 'Cremophor' RH60 (200 g.) | |
| 'Mulgofen' EL 719 (200 g.) | (a polyoxyethylated vegetable oil) |
| 'Tween' 40 (200 g.) | |
| 'Tween' 80 (200 g.) | |

The resulting solution is sterilised by the procedure described in either Example 1 or Example 2 and there is thus obtained a sterile solution suitable for parenteral administration to a warm-blooded animal.

EXAMPLE 9

A stirred mixture of 2,6-diisopropylphenol (2 g.), polyethylene glycol 200 (10 g.) and 'Cremophor' RH40 (10 g.) is gently heated until a homogeneous mixture is obtained. Water for injection (78 g.) is added portionwise, and the resulting clear solution is sterilized by passage through a bacterial filter (cellulose ester membrane, pore size 0.22μ.). There is thus obtained a sterile composition suitable for parenteral administration to a warm-blooded animal.

The process described above is repeated using the following ingredients:
a. 2,6-diisopropylphenol (2 g.); ethanol (5 g.); 'Cremophor' EL (10 g.); water (to 100 g.).
b. 2,6-diisopropylphenol (2 g.); propylene glycol (10 g.); 'Cremophor' EL (10 g.); water (to 100 g.).
c. 2,6-diisopropylphenol (2 g.); polyethylene glycol 400 (10 g.); 'Cremophor' EL (10 g.); water (to 100 g.).
d. 2,6-diisopropylphenol (2 g.); polyethylene glycol 600 (10 g.); 'Cremophor' EL (10 g.); water (to 100 g.).
e. 2,6-diisopropylphenol (2 g.); ethanol (5 g.); 'Cremophor' RH40 (20 g.); water (to 100 g.).
f. 2,6-diisopropylphenol (2 g.); propylene glycol (10 g.); 'Cremophor' RH40 (20 g.); water (to 100 g.).
g. 2,6-diisopropylphenol (2 g.); polyethylene glycol 200 (10 g.); 'Cremophor' RH40 (20 g.); water (to 100 g.).
h. 2,6-diisopropylphenol (2 g.); ethanol (10 g.); 'Tween' 60 (10 g.); water (to 100 g.).
i. 2,6-diisopropylphenol (2 g.); ethanol (8 g.); 'Tween' 20 (polyoxyethylene (20) sorbitan monolaurate (15 g.); water (to 100 g.).

There are thus similarly obtained sterile compositions suitable for parenteral administration to a warm-blooded animal.

EXAMPLE 10

A solution of 2,6-diisopropylphenol (2 g.) in ethanol (10 g.) is added to a stirred solution of polyoxyethylene (23) lauryl ether ('Brij' 35) (20 g.) in water for injection (20 g.), and further water for injection (48 g.) is then added. The mixture thus obtained is sterilized by heating in a steam autoclave at 115° C. for 30 minutes, and there is thus obtained a sterile composition suitable for parenteral administration to a warm-blooded animal.

The process described above is repeated except that there are used as ingredients:
a. 2,6-diisopropylphenol (2 g.); propylene glycol (10 g.); polyoxyethylene-polyoxypropylene block copolymer; 'Pluronic' F68 (10 g.); water (to 100 g.).
b. 2,6-diisopropylphenol (2 g.); ethanol (20 g.); polyvinylpyrrolidone ('Plasdone' C 15) (30 g.); water for injection (to 100 g.).

There are thus similarly obtained sterile compositions suitable for parenteral administration to a warm-blooded animal.

EXAMPLE 11

Water for injection is added slowly to a stirred solution of 2,6-diisopropylphenol (2 g.) in ethanol (40 g.) until the total weight of the mixture is 100 g. The mixture is then sterilized by passage through a bacterial filter and there is thus obtained a sterile composition suitable for parenteral administration to a warm-blooded animal.

The process described above is repeated except that the 40 g. of ethanol is replaced by 70 g. of either propylene glycol, polyethylene glycol 200, polyethylene glycol 400 or polyethylene glycol 600. There are thus similarly obtained sterile compositions suitable for parenteral administration to a warm-blooded animal.

EXAMPLE 12

2,6-Diisopropylphenol (2 g.) is added to a stirred solution of saccharin sodium (5 g.) in water for injection (93 g.). The solution thus obtained is sterilized by passage through a bacterial filter and there is thus obtained a sterile composition suitable for parenteral administration to a warm-blooded animal.

The process described above is repeated except that a cyclodextran (Schardinger α-dextrin) (4 g.) is used in place of the 5 g. of saccharin sodium. There is thus similarly obtained a sterile composition suitable for parenteral administration to a warm-blooded animal.

EXAMPLE 13

A mixture of 2,6-diisopropylphenol (2 g.), propylene glycol (10 g.) and 'Cremophor' EL (10 g.) is warmed until a clear solution is obtained. The solution is sterilized by passage through a bacterial filter and there is thus obtained a concentrated sterile solution suitable for dilution with sterile water in order to form a sterile composition suitable for parenteral administration to a warm-blooded animal.

The process described above is repeated except that there is also incorporated a silicone antifoaming agent (0.001 g.). There is thus similarly obtained a concentrated sterile solution suitable for dilution as stated above.

EXAMPLE 14

The process described in Example 1 is repeated except that the distilled water is replaced by an equal volume of 0.9% w/v aqueous sodium chloride solution ("physiological saline"). There is thus obtained a 2% sterile solution suitable for parenteral administration to a warm-blooded animal.

The 2% sterile solution described above is diluted with an equal volume of "physiological saline." There is thus obtained a 1% sterile solution suitable for parenteral administration to a warm-blooded animal.

EXAMPLE 15

Each mouse in various groups of 10 mice is injected intravenously with a 1% sterile solution of 2,6-diisopropylphenol as described in Example 14, the total dose administered being the same within any group but differing between groups. The dose ($HD_{50}$) required to cause anaesthesia (loss of righting reflex for at least 30 seconds) in 5 out of 10 mice, and the dose ($LD_{50}$) required to kill 5 out of 10 mice, are then determined to be 13.5 mg./kg. bodyweight and 56 mg./kg. bodyweight respectively. The therapeutic ratio ($LD_{50}/HD_{50}$) is therefore 4.14.

Each of 10 mice is injected intravenously with 27 mg./kg. bodyweight (twice the $HD_{50}$) of 2,6-diisopropylphenol as a 1% sterile solution described in Example 14. The mean sleeping time of a mouse is 4.29 minutes (standard deviation ± 0.59 minutes).

For comparison, under similar conditions using the known anaesthetic agent thiopentone sodium, the corresponding figures are:

| | |
|---|---|
| $HD_{50}$ | 23.5 mg./kg. bodyweight |
| $LD_{50}$ | 100 mg./kg. bodyweight |
| Therapeutic ratio | 4.26 |
| Mean sleeping time after twice the $HD_{50}$ | 5.97 ± 1.63 minutes |

EXAMPLE 16

A 2% sterile solution of 2,6-diisopropylphenol prepared as described in Example 14 is administered intravenously to a pigtail monkey weighing 6.8 kg. at a rate of 0.05 mg. of phenol/kg. bodyweight/second until a dose of 34 mg. (5 mg./kg. bodyweight) of the phenol has been injected. Induction of anaesthesia is smooth and rapid, muscle relaxation is produced, spinal reflexes are depressed and anaesthesia lasts for approximately 6 minutes. Recovery after this period is rapid and is almost complete 16 minutes after induction.

EXAMPLE 17

A 2% sterile solution of 2,6-diisopropylphenol prepared as described in Example 14 is administered intravenously to each cat in a group of 5 cats, at a rate of 0.05 mg. of phenol/kg. bodyweight/second, until each cat has received a dose of 10 mg. of phenol/kg. bodyweight. Induction of anaesthesia is rapid and free from excitment, muscle relaxation is produced and spinal reflexes are depressed. Response to painful stimulation returns after approximately 10 minutes, and further recover is smooth and rapid. Righting reflexes reappear after a mean time of 34 minutes (standard deviation ± 7.35 minutes) from induction and the cat is able to stand again after a mean time of 42.6 minutes (± 10.29 minutes) after induction.

EXAMPLE 18

A cat weighing 2.5 kg. is anaesthetised exactly as described in Example 17. A laparotomy operation is then begun which lasts for 45 minutes, and anaesthesia is maintained during that time by four supplementary intravenous injections each of 2.0 mg. of phenol/kg. bodyweight administered as a 2% sterile solution. After the operation recovery is rapid and the cat is able to stand 35 minutes after completion of the operation.

EXAMPLE 19

A cat is anaesthetised exactly as decribed in Example 17. Anaesthesia is produced of sufficient depth to allow intubation of the trachea following the application of a topical anaesthetic to the larynx. Anaesthesia is thereafter maintained with an inhalation anaesthetic delivered through an Ayre's T-piece circuit.

EXAMPLE 20

A 2% sterile solution of 2,6-diisopropylphenol prepared as described in Example 14 is injected intramuscularly into a cat at a dose of 35 mg. of phenol/kg. bodyweight. Righting reflexes are lost after 15 minutes, and after a further 25 minutes anaesthesia has deepened sufficiently to allow intubation to be carried out. Muscle tone returns after a further 60 minutes and thereafter recovery is uneventful. No pain or lesion at the site of injection is observed during the subsequent 7 days.

EXAMPLE 21

Distilled water is added to a solution of 2,6-diisopropylphenol (20 g.) in a polyoxyethylated castor oil ('Texofor' D40) (150 g.) until a volume of 1 liter is obtained. The solution is filled into ampoules each containing 10 ml. of solution, and the ampoules are sealed and sterilized by heating in a steam autoclave at 115° C. for 30 minutes. There is thus obtained a sterile composition suitable for parenteral administration to a warm-blooded animal.

EXAMPLE 22

The process described in Example 21 is repeated except that there are used as ingredients:

2,6-diisopropylphenol (20 g.)

'Cremophor' RH40 (140 g.)

distilled water (to 1 liter)

Sufficient sodium chloride is added to make the solution isotonic with blood, and the pH of the solution is adjusted to 6 with citric acid. The solution is filled into ampoules and sterilized as described in Example 21, and there is thus obtained a sterile composition suitable for parenteral administration to a warm-blooded animal.

EXAMPLE 23

The process described in Example 9 is repeated except that there are used as ingredients:
2,6-diisopropylphenol (2 g.)
ethanol (10 g.)
'Cremophor' RH40 (10 g.)
water (to 100 g.)

There is thus obtained a sterile composition suitable for parenteral administration to a warm-blooded animal.

What we claimed is:

1. A method for producing anaesthesia in a warm-blooded animal which comprises administering parenterally to said animal an anaesthetically effective amount of 2,6-diisopropylphenol.

2. The method claimed in claim 1 wherein there is administered intravenously between 2.5 and 10 mg. of 2,6-diisopropylphenol per kg. bodyweight of the animal.

UNITED STATES PATENT AND TRADEMARK OFFICE

CERTIFICATE EXTENDING PATENT TERM
UNDER 35 U.S.C. 156

Patent No.    : 4,056,635

Dated         : November 1, 1977

Inventor(s)   : John Baird Glen et al

Patent Owner  : Imperial Chemical Industries PLC

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 26th day of November 1990.

Harry F. Manbeck, Jr.
Assistant Secretary and Commissioner
  of Patents and Trademarks